United States Patent [19]
Rothenberg et al.

[11] Patent Number: 5,666,958
[45] Date of Patent: Sep. 16, 1997

[54] INTERFACE MODULE FOR ELECTRICALLY CONNECTING MEDICAL EQUIPMENT

[76] Inventors: Peter M. Rothenberg, 8 Cobblestone Ct., Laguna Niguel, Calif. 92677; Kent Melancon, 26205 Via de Gavilan, San Juan Capistrano, Calif. 92675

[21] Appl. No.: 418,663

[22] Filed: Apr. 6, 1995

[51] Int. Cl.⁶ .................................................. A61B 5/0416
[52] U.S. Cl. .............................................. 128/696; 439/909
[58] Field of Search .............................. 607/1, 2, 10, 36, 607/37, 63, 115; 128/642, 696, 697, 709, 710, 908; 439/173, 177, 569, 620, 638, 654–5, 854–5, 909

[56] References Cited

U.S. PATENT DOCUMENTS

| | | | |
|---|---|---|---|
| 3,605,728 | 9/1971 | Ogle | 128/908 X |
| 3,920,005 | 11/1975 | Gombrich et al. | |
| 4,088,138 | 5/1978 | Diack et al. | |
| 4,368,363 | 1/1983 | Ahuja | 439/638 X |
| 4,387,717 | 6/1983 | Brownlee et al. | |
| 4,527,567 | 7/1985 | Fischler et al. | |
| 4,532,934 | 8/1985 | Kelen | |
| 4,550,731 | 11/1985 | Batina et al. | |
| 4,619,275 | 10/1986 | Ross et al. | 607/2 |
| 4,658,831 | 4/1987 | Reinhard et al. | |
| 4,705,042 | 11/1987 | Giurtino | |
| 4,744,369 | 5/1988 | Kroll | 128/908 X |
| 4,834,677 | 5/1989 | Archang | 439/638 X |
| 4,858,617 | 8/1989 | Sanders | |
| 4,892,102 | 1/1990 | Astrinsky | |
| 5,016,634 | 5/1991 | Vock et al. | |
| 5,105,809 | 4/1992 | Bach, Jr. et al. | |
| 5,158,078 | 10/1992 | Bennett et al. | |
| 5,209,228 | 5/1993 | Cano et al. | |
| 5,222,493 | 6/1993 | Sholder | |
| 5,231,990 | 8/1993 | Gauglitz | |
| 5,233,985 | 8/1993 | Hudrlik | |
| 5,233,986 | 8/1993 | Robson | |
| 5,243,981 | 9/1993 | Hudrlik | |
| 5,276,443 | 1/1994 | Gates et al. | 439/620 X |
| 5,309,919 | 5/1994 | Snell et al. | |
| 5,341,812 | 8/1994 | Allair et al. | 128/696 |
| 5,433,732 | 7/1995 | Hirschberg et al. | 128/908 X |

FOREIGN PATENT DOCUMENTS 596344  5/1994  European Pat. Off. .

OTHER PUBLICATIONS

"Bard Critical Care Bipolar Temporary Transvenous Pacing Electrode" direction booklet, Rev. 2/3–89/5014371, C.R. Bard, Inc., Tewksbury, MA.

*Primary Examiner*—Jeffrey R. Jastrzab
*Attorney, Agent, or Firm*—Donald E. Stout

[57] ABSTRACT

A temporary transvenous pacing system for obtaining a graphical record verifying the placement of temporary cardiac pacing lead within the ventricular cavity of a heart and for intracardiac recordings for arrythmia diagnosis. The system includes a temporary transvenous pacing lead having a distal electrode which terminates in a standard connector. A physiological monitor includes sensing electrodes having at least one connector adapted for electrical connection to a body surface. An interface module includes connectors adapted to interconnect the pacing lead to the monitor, and a coupling circuit for conditioning the pacing lead signals for use by the monitor. The pacing lead signals are displayed on an oscilloscope screen of the monitor, whereby an attending physician may adjust the pacing lead position in response to the electrical waveforms so obtained.

17 Claims, 3 Drawing Sheets

INTERFACE MODULE FOR ELECTRICALLY CONNECTING MEDICAL EQUIPMENT

BACKGROUND OF THE INVENTION

1. Field of the Invention

The present invention is directed generally to an apparatus for verifying the correct position of a temporary transvenous cardiac pacing lead in the ventricular cavity of a heart prior to emergency pacing, and more particularly to a system allowing visual inspection of pacing lead position by direct electrical connection between the temporary pacing lead and a conventional ICU physiological monitor. It may also be used to facilitate random intracardiac recordings of rhythm.

2. Description of The Related Art

Medical instrumentation for the care and monitoring of the critically ill cardiac patient has improved significantly over the last decade, due in part to improved design and operability of temporary cardiac pacing leads and cardiac monitors such as the conventional electrocardiograph (ECG). Continuous monitoring of a cardiac patient's condition allows a physician to take immediate corrective action in the event of a highly irregular heartbeat or a heart attack.

When a cardiac patient suffers an arrythmia of the type requiring intervention of an internal pacing system, a physician will typically insert a temporary pacing lead into the heart cavity which functions to exogenously stimulate the myocardium, increasing a dangerously slow rhythm or over-riding and controlling a dangerously fast one. The temporary pacing lead is generally inserted into the heart chamber percutaneously with either fluoroscopic or electrocardiographic guidance. The pacing lead is directed along a path through the superior vena cava or inferior vena cava, right atrium, across the tricuspid valve and into the right ventricle where it is positioned abutting the ventricular wall. The close proximity of the pacing electrode to the ventricular wall is mandatory as any increase of this distance poses a risk of failure of the electrode to capture the heart muscle (myocardium) and hence reoccurrence of the patient's initial arrhythmia.

In order to correctly position the pacing lead against the ventricular wall, the lead is configured as a sensing electrode which is connected to the voltage lead of an electrocardiograph so that the characteristic electrical signals representing the complex electrical operation of the heart may be examined by the attending physician. By assessing the relative sizes and shapes of the P-wave and QRS complex signals, the physician is able to accurately determine the position of the pacing lead within the heart. Once the pacing lead is correctly positioned, heart pacing by means of an external power source may begin.

However, an electrocardiograph is a costly, complex, and highly specific piece of medical equipment which must be operated by a skilled technician. Consequently, undue delay may be incurred in responding to a cardiac emergency because either an electrocardiograph or a technician is unavailable at the time of the emergency.

In many hospitals, intensive care (ICU) and/or cardiac care (CCU) facilities have been designated for the care of critical or cardiac patients. These facilities are equipped with devices adapted to monitor the patient's vital signs (e.g., heart rate, respiratory rate, blood pressure, etc.) and provide a telemetric link between each patient and a multi-purpose physiological monitoring unit termed an ICU monitor. Vital sign data is derived through spaced apart skin contact electrodes, disposed about the body, which sense the minute voltage changes accompanying physiological activity. The sensed voltage changes are amplified and displayed on an oscilloscope type screen for easy visual inspection. ICU monitors are generally available. However, the nature of the electrical connectors of the pacing lead and the ICU monitor sensing leads differ substantially from each other.

Pacing lead connectors are elongated rigid conductors adapted for bayonet-type insertion into the mating plug of a cardiac stimulation battery, and in some cases the voltage sensing lead of an electrocardiograph machine. In contrast, ICU monitors typically employ a five-way standard lead configuration with unipolar electrodes. One of the electrodes is attached adjacent the lower right ribcage of the patient as a signal reference, while monitor signals are developed as potential differences between associated pairs of additional electrodes. The electrodes themselves are generally circular, and contact the body at a concave surface through a silver compound applied to the skin. Electrical connection to the ICU monitor is made by a flanged snap fit connector which engages a mating member extending outward from the electrode's upper surface.

In addition, many ICU monitors are configured for receiving a voltage input, which requires that signals induced into the sensing leads be dropped across an associated impedance. Since the electrical signals transmitted by a pacing lead to an external device are invariably current signals, pacing lead impedances are strictly limited. In most cases, the impedance values of the entire lead may not exceed 30 ohms. Consequently, the nature of the electrical signals provided by a pacing lead and those required by an ICU monitor may be substantially incompatible as well.

It is known to utilize an alligator clip in an attempt to electrically couple the appropriate sensing lead of the monitor with an oscilloscope. However, this is typically not a stable connection, and the alligator clip may not have the correct electrical characteristics to enable the oscilloscope to properly display accurate signals from the myocardium. In addition, the pacing lead has a proximal terminal which is exposed and this presents a potential danger to the patient.

SUMMARY OF THE INVENTION

The present invention is directed to overcoming one or more of the difficulties discussed above. Accordingly, the present invention establishes direct electrical communication between a temporary pacing lead and a conventional ICU monitor. The invention enables an ICU monitor to display signals from a pacing lead allowing a physician to assess the location of the pacing lead within the heart chambers without fluoroscopy or EKG monitoring. ICU monitors are available at a patient's bedside in virtually all ICU wards, and unlike electrocardiograph machines or fluoroscopy do not require extensive additional equipment or highly trained technicians.

In one aspect, the present invention is directed to an apparatus for verifying the placement of a temporary cardiac pacing lead within the ventricular cavity of a heart or facilitating random intracardiac recordings for arrythmia diagnostic purposes. The apparatus comprises a monitor, a temporary transvenous pacing lead and an interface module. The monitor, which is preferably an ICU monitor, includes a plurality of sensing leads at least one of which is adapted for electrical connection to a body surface. That sensing lead has a first type connector of one gender. The temporary transvenous pacing lead has a proximal and distal electrode for pacing or for sensing electrical signals associated with myocardial depolarization and a second type connector of one gender adapted for connection of either electrode to an electrocardiograph mating receptacle or power source. The interface module establishes electrical communication between the ICU monitor and the temporary transvenous pacing lead so that the monitor can display the signals from one of the two electrodes. As the distal electrode is used for pacing, generally it is the one used for recordings.

Although the interface module can be of various different constructions, it preferably includes a supporting structure, a third connector carried by the supporting structure for mating with a respective connector of a selected one of the plurality of sensing leads of the ICU monitor, a fourth connector carried by the supporting structure for mating with the connector of the temporary transvenous pacing lead, and a coupling circuit electrically connecting the third and fourth connectors. In a preferred construction, the supporting structure includes a housing. The third connector is preferably mounted on an exterior surface of the housing where it is easily accessible for connection to the connector of the monitor. The coupling circuit and at least a portion of the fourth connector are preferably mounted within the housing.

Another feature of this invention is that the coupling circuit may include a resistor to condition the sensed electrical signals received from the temporary transvenous pacing lead for use by the ICU monitor. This enables ICU monitors of different types to be used for signal display purposes.

A common pacing lead second type connector comprises an elongated substantially rigid pin-type conductive member, disposed at an end opposite the distal electrode, and adapted for bayonet-type insertion into a mating receptacle. The ICU monitor sensing lead first type connector typically comprises a flanged receptacle for snap-fit connection to a mating member. The third connector preferably has a waist section for engaging the receptacle flange, thereby releasably securing the receptacle to the third connector and making electrical connection therebetween.

The interface module preferably includes a receptacle for receiving and electrically insulating the proximal terminal of the pacing lead. By so doing, the risk of electrical shock to the patient is reduced.

These and other features and advantages of the invention can be better understood from the following detailed description, taken in conjunction with the accompanying illustrative drawings.

DESCRIPTION OF THE PREFERRED EMBODIMENT

Figure 1:
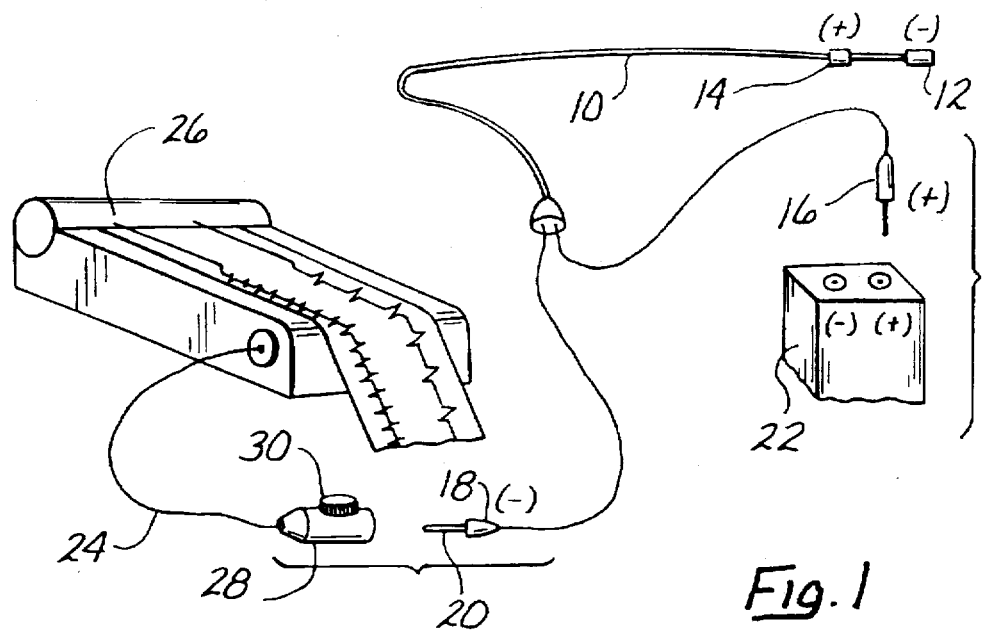
FIG. 1 depicts a temporary cardiac pacing lead and associated ECG and stimulus source connections in accordance with the prior art.

Referring now to FIG. 1, there is shown a prior art temporary intracardiac pacing system which includes a temporary transvenous pacing lead 10 of the type manufactured by C. R. Bard Incorporated of Tewksbury, Mass. The pacing lead includes a distal electrode 12 (marked −) at the tip of the lead which is used for supplying pacing pulses to the heart and for relaying electrical signals resulting from myocardial depolarization. The pacing lead also includes a proximal electrode 14 (marked +) located axially along the lead at a distance of approximately 1 centimeter from the distal electrode. Each electrode is connected by conductive wires to respective pin-type connector or jacks 16 and 18 which functionally connect the pacing lead electrodes to external instrumentation. The connectors 16 and 18 are constructed of an elongated pin shaped conductive member 20 electrically bonded to the electrode wire. A non-conductive housing is provided at the joint between the conductive pin and the electrode wire for supporting the joint and for providing a means to grasp the connector.

In a typical pacing application, the proximal electrode 14 is connected to a positive terminal of an external pulse generator 22 or power source by inserting connector 16, which constitutes a proximal terminal, into a respective positive mating plug. Likewise, the distal electrode 12 is connected to a negative terminal of the pulse generator 22 by inserting connector 18 into a respective negative mating plug.

In an application where the pacing lead is to be used for intracardiac sensing, the negative connector 18 is connected to an electrocardiograph voltage sensing lead 24 connected, in turn, to an electrocardiograph 26 for visually monitoring the electrical activity of the heart.

Connector 18 is connected to the electrocardiograph voltage sensing lead 24 by an alligator clip (not shown) or by inserting conductive pin 20 into a longitudinal mating cavity provided within a housing 28. A set screw 30 is threaded through the housing and into the cavity so that by tightening the screw, pin 20 is securely fastened in the cavity and electrical contact is established therebetween. The electrocardiograph is then used to provide a graphical record of cardiac electrical signals sensed by the pacing lead electrode.

Figure 2:
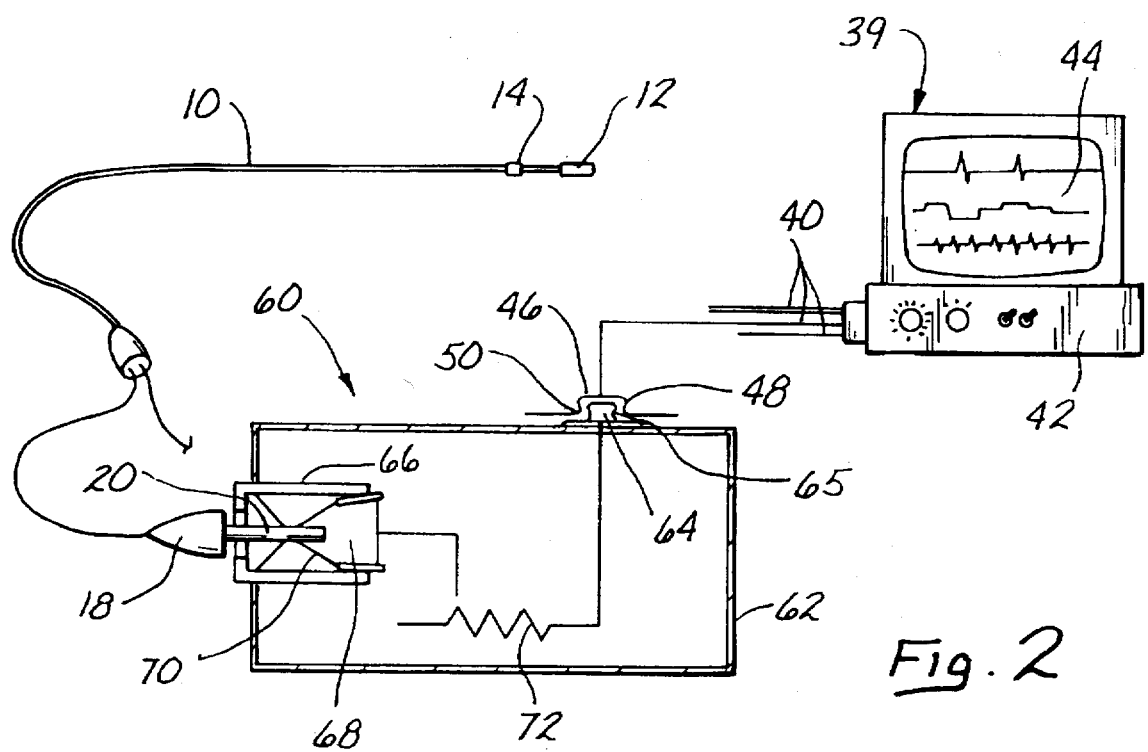
FIG. 2 depicts a system constructed in accordance with this invention.

FIG. 2 depicts a physiological monitor or ICU monitor 39 of the type commonly provided at a patient's bedside in an intensive care (ICU) hospital ward. The monitor 39 includes a plurality of sensing electrodes 40, which are adapted for connection to various physiological sensing devices, such as blood pressure cuffs, heart rate and respiratory sensors, and the like (not shown), attached to the body of the patient. The electrodes 40 are connected, in turn, to a signal amplification and processing unit 42. Minute current and voltage signals received from the body by the sensing electrodes are amplified by processing unit 42 and processed for display on an oscilloscope-type screen 44 provided for visual monitoring of physiological functions.

One of the sensing electrodes 40, which is an ECG lead, terminates in a female connector 46 adapted for snap-fit connection to a mating connector of opposite gender provided on a sensing device. Connector 46 is suitably constructed of a generally disk shaped conductive material which includes a central cavity portion 48. The cavity's interior wall is uniformly necked down into the cavity throat, thereby defining an inwardly extending circumferential flange 50 for receiving a mating connector post.

Figure 3:
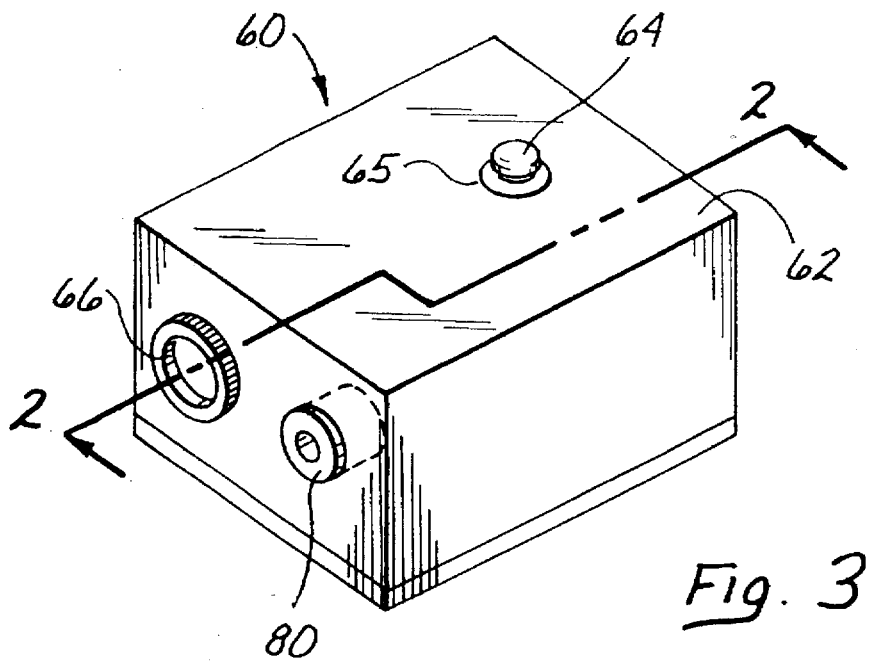
FIG. 3 is a perspective view of one form of an interface module of this invention.

In FIG. 3, there is depicted an interface module 60 for providing a direct electrical connection between the temporary transvenous pacing lead 10 and a physiological monitoring device, such as the ICU monitor 39.

Interface module 60 suitably comprises a supporting structure, which in the illustrated embodiment, is in the form of a rectangular, box shaped, supporting housing 62 constructed of a rigid material such as plastic or metal. A snap-fit connector 64, of a gender opposite that of, and for mating with, a respective ICU monitor sensing lead connector 46, is provided on an exterior surface of the housing. Connector 64, which is a male connector, communicates with the interior of the interface module through an opening cut into the surface of the housing and over which the connector is mounted. Connector 64 includes a conductive post extending outwardly from the housing surface. The post is generally cylindrical in shape, and includes a circumferential indentation or waist section 65, formed in a region of the post proximate to the housing surface end. An ICU monitor sensing lead connector, such as connector 46 of FIG. 2, adapted for connection to a physiological sensing device, may be pressed onto snap-fit connector 64. The sensing lead connector flange 50 engages the circumferential indentation 65 of snap-fit connector 64, thereby releasably securing the connectors together and effectuating electrical contact therebetween.

The module 60 also includes a female or receptacle connector 66 for mating with the pin-type pacing lead connector jack 18. Receptacle connector 66 includes a mating cavity 68, disposed, at least partially, within the housing. Conductive leaf-spring terminals 70 extend into the mating cavity 68 and comprise a spring-loaded clamp to exert a friction force on the conductive pin 20 of the pacing lead connector jack 18, thereby releasably securing the pin in the receptacle and making electrical contact therewith.

A coupling circuit 72 is connected between the conductive leaf-spring terminals 70 of connector 66 and the underside of snap-fit connector 64, thereby completing the electrical circuit between the pacing lead electrode 12 and the monitor display 44. In the illustrated embodiment, coupling circuit 72 comprises a variable resistor, selectably variable between resistance values of zero ohms to about several thousand ohms. Coupling circuit 72 is provided in order to condition the electrical signals received by the pacing lead electrode 12 for use by a variety of amplification and processing units 42 included in physiological monitors. Sensing electrode signals are typically voltage signals which often include far-field and noise components that must be removed from the signal in order to reveal the myocardial signals of interest. In addition, physiological monitors are manufactured with a variety of electrical input configurations. Coupling circuit 72 insures compatibility between the pacing lead signal and grounded or ungrounded, voltage or current configured monitor inputs. In the preferred embodiment, coupling circuit 72 is set to a value of 1000 ohms.

Although the coupling circuit 72 in the illustrated embodiment has been shown as a variable resistor, various alternatives may be suitably employed by one skilled in the art. For example, a fixed resistor may be used, with a value chosen to match the input requirements of a particular model of physiological monitor unit. The fixed resistor may be connected alone, in serial fashion between the connectors 46 and 66, or connected in parallel with a straight-wire connector, and switched into and out of the circuit by an appropriate selector switch.

The interface module 60 also includes a receptacle 80 for receiving and electrically insulating the proximal terminal 16 to provide electrical isolation for the terminal. The receptacle 80 is preferably constructed of a suitable electrical insulating material, such as a polymeric material, thereby holding the receptacle out of electrical contact with the coupling circuit 72. Of course, other techniques which will keep the proximal terminal 16 out of electrical contact with the coupling circuit 72 may be employed, if desired.

In operation of the temporary pacing system, the connectors 18 and 16 of the temporary pacing lead 10 are connected to the receptacle connector 66 and the receptacle 80, respectively, of the interface module 60 as described above. The appropriate one of the sensing electrodes 40 of the monitor 39 is connected to the connector 64 of the interface module 60, thus establishing electrical communication between the monitor and the sensing electrode of the pacing lead.

Figure 4:
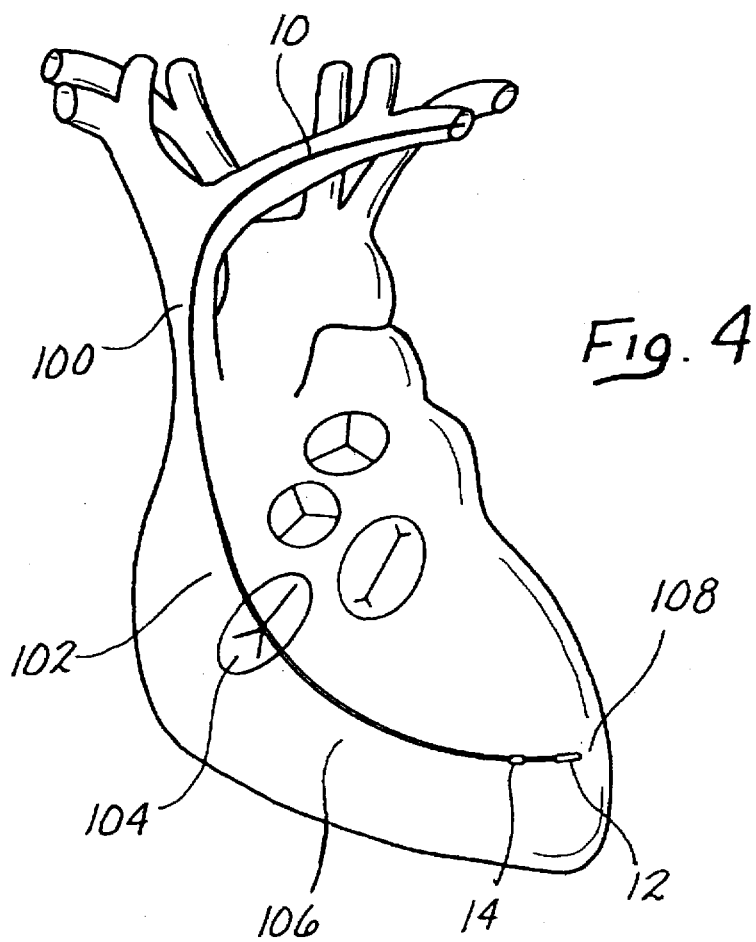
FIG. 4 is a schematic view of a heart showing the insertion path of a transvenous pacing lead.

For intracardiac sensing, the pacing lead 10 is inserted, for example, into the sub-clavian vein through an incision made below the left clavicle of the cardiac patient. As depicted in FIG. 4, the pacing lead 10 is threaded through the sub-clavian vein and superior vena cava 100, then enters the heart at the right atrium 102. As insertion continues, the lead 10 travels into and traverses the right atrium 102, moves through the tricuspid valve 104, separating the right atrium from the right ventricle 106 and, in a proper insertion, comes to rest in contact with the endocardial wall 108 of the right ventricle. With the distal electrode 12 in proper position against the ventricle wall, the pacing lead 10 may then be connected to a conventional external pacemaker and ventricular pacing may proceed normally.

Position dependent electrical signals, caused by ventricular and atrial depolarization and repolarization, are sensed by the distal sensing electrode and displayed on the ICU monitor screen 44. An attending physician relies on the size and shape of the various components of these signals to determine if the pacing lead is in the proper position for pacing. This same basic procedure may be used to evaluate the atrial and ventricular components to arrhythmias.

Figure 5:
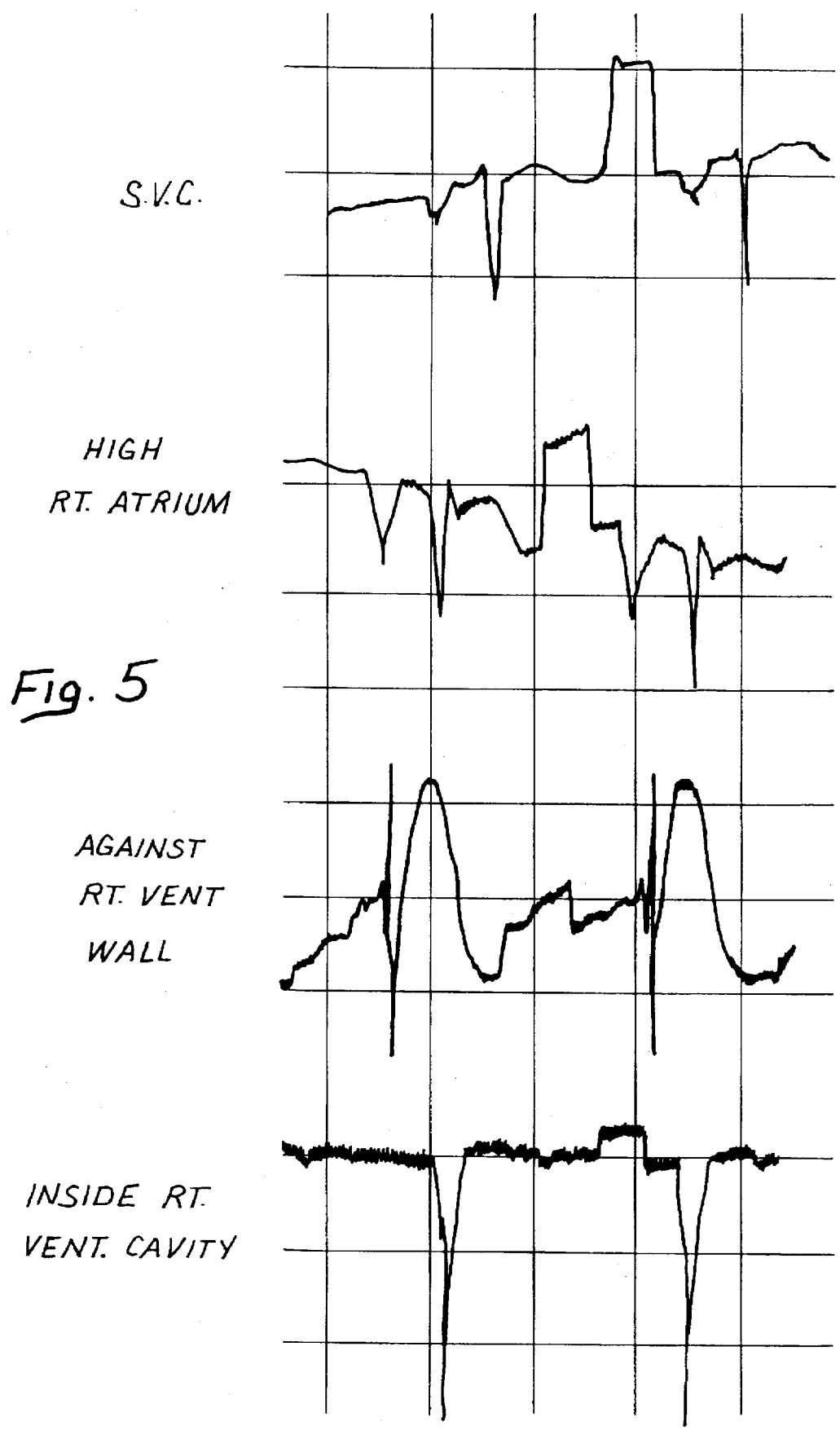
FIG. 5 is a waveform diagram illustrating ECG signals obtained when the pacing lead is in various locations in the heart.

FIG. 5 depicts electrocardiogram traces, displayed on the monitor screen 44, illustrating the signals obtained when the distal sensing electrode of the pacing lead 10 is located in the heart portions identified in connection with FIG. 4. The upper trace in FIG. 5 represents an electrocardiographic signal obtained when the distal electrode 12 is located in the superior vena cava 100 (FIG. 4). Similarly, the second, third and a lower traces in FIG. 5 represent an electrocardiogram signal obtained when the distal electrode 12 is located in the high right atrium, the right ventricle and when the distal electrode 12 is in contact with the ventricular wall, respectively.

By reason of the distinct and easily detectable differences in the signal components produced when the sensing electrode of a pacing lead moves through the heart, the location of the pacing lead may be accurately determined and adjusted by reference to those signal components. By graphically displaying the signals on an oscilloscope screen of an ICU monitor, these signals are made easily accessible to an attending physician.

While a particular embodiment of the invention has been shown and described, changes and modifications may be made without departing from the invention in its broader aspects which should be limited only by the scope of the appended claims.

What is claimed is:

1. An interface module for direct electrical connection between an ICU monitor and a temporary transvenous pacing lead, the module comprising:

a housing;

a first electrical connector disposed on an exterior surface of said housing for mating with a respective electrical connector of a selected one of a plurality of sensing leads of the ICU monitor;

a second electrical connector for mating with an electrical connector of the temporary transvenous pacing lead, at least a portion of said second connector being disposed within said housing; and a coupling circuit electrically connected between the first and second electrical connectors.

2. The module of claim 1, wherein the coupling circuit includes a resistor.

3. The module of claim 1, wherein the first electrical connector is a male connector and has an indented waist section.

4. The module of claim 1, wherein the second connector includes a receptacle for receiving the pacing lead connector.

5. The module of claim 1, wherein the second connector comprises a spring-loaded clamp for gripping the pacing lead connector.

6. The module of claim 1, wherein the coupling circuit includes a variable resistor.

7. The module of claim 6, wherein the variable resistor is selectively variable between resistance values of zero ohms to about several thousand ohms.

8. The module of claim 6, wherein the coupling circuit is set to a value of about 1000 ohms.

9. The module of claim 1, wherein the first connector is a snap-fit connector.

10. The module of claim 1, and further comprising a receptacle within said housing and carried by said housing, said receptacle opening at the external surface of the housing for receiving a second electrical connector terminal of said temporary transvenous pacing lead.

11. An interface module, comprising:

a housing having an external surface and an interior chamber;

a male electrical connector carried on the exterior surface of the housing;

a female electrical connector within said housing and carried by said housing;

a receptacle within said housing and carried by said housing, said receptacle opening at the external surface of the housing for receiving an electrical connector of a medical instrument;

a coupling circuit including a resistor coupling the male electrical connector and the female electrical connector; and said receptacle being always out of electrical contact with said coupling circuit.

12. The interface module of claim 11, wherein said resistor comprises a variable resistor.

13. The interface module of claim 11, wherein the male connector is a snap-fit connector having an indented waist section.

14. The interface module of claim 11, wherein the female connector comprises a spring-loaded clamp.

15. An interface module for direct electrical connection between an ICU monitor and medical equipment having an electrical connector, the module comprising:

a supporting structure;

a first snap-fit electrical connector having an indented waist section, said first connector carried by the supporting structure for mating with a respective electrical connector of a selected one of a plurality of sensing leads of the ICU monitor;

a second electrical connector carried by the supporting structure for mating with the electrical connector of the medical equipment; and a non-current limiting coupling circuit including a resistor, said coupling circuit being electrically connected between the first and second electrical connectors.

16. The module of claim 15, wherein the resistor comprises a variable resistor and is selectively variable between resistance values of zero ohms to about several thousand ohms.

17. The module of claim 15, and further comprising a receptacle within said structure and carried by said structure, said receptacle opening at an external surface of the structure for receiving an electrical connector terminal of said medical equipment.

* * * * *